(12) United States Patent
Slocik et al.

(10) Patent No.: US 11,781,106 B1
(45) Date of Patent: Oct. 10, 2023

(54) INTRACELLULAR NON-GENETIC MODIFICATION OF MICROORGANISMS USING PROTEIN IONIC LIQUIDS

(71) Applicant: Government of the United States, as represented by the Secretary of the Air Force, Wright-Patterson AFB, OH (US)

(72) Inventors: Joseph M Slocik, Dayton, OH (US); Rajesh R. Naik, Centerville, OH (US); Patrick B Dennis, Cincinnati, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 17/187,976

(22) Filed: Mar. 1, 2021

(51) Int. Cl.
  *C12N 1/20*     (2006.01)
  *C12N 15/87*    (2006.01)
  *C07K 17/02*    (2006.01)
  *C12N 9/96*     (2006.01)

(52) U.S. Cl.
  CPC .............. *C12N 1/20* (2013.01); *C07K 17/02* (2013.01); *C12N 9/96* (2013.01); *C12N 15/87* (2013.01)

(58) Field of Classification Search
  CPC . C12N 9/96; C12N 1/20; C12N 15/87; C12N 11/02; C07K 17/02
  See application file for complete search history.

(56) References Cited

FOREIGN PATENT DOCUMENTS

WO   WO-2010025859 A2 *   3/2010   .............. A01N 1/021
WO   WO-2011056545 A2 *   5/2011   .......... A61K 31/4196

OTHER PUBLICATIONS

Sharma et al. "Antibacterial and Antifungal Activity of Biopolymers Modified with Ionic Liquid and Laponite", 2015, Appl Biochem Biotechnol, vol. 177, p. 267-277. (Year: 2015).*
Thuy Pham et al. "Environmental fate and toxicity of ionic liquids: A review", 2010, Water Research, vol. 44, p. 352-372. (Year: 2010).*
Reslan and Kayser, "Ionic liquids as biocompatible stabilizers of proteins", 2018, Biophysical Reviews, vol. 10, p. 781-793. (Year: 2018).*

* cited by examiner

*Primary Examiner* — Gary B Nickol
*Assistant Examiner* — Amelia Nicole Dickens
(74) *Attorney, Agent, or Firm* — AFMCLO/JAZ; Timothy M. Barlow

(57) ABSTRACT

A method for transfecting microorganisms comprises inoculating a growth media consisting of at least one of sterile LB media and tryptic soy broth with microorganism cells (cells) consisting of at least one of *E.coli* (DH5α), *C. lytica*, or *B. subtilus, Pichia pastoris*; growing the cells at between 28-40° C. to achieve a desired cell density; harvesting the cells; adding a protein ionic liquid consisting of at least one of green fluorescent protein (GFP), ferritin, rabbit IgG antibodies, and photosystem II from spinach ionic liquid to the cells; suspending the cells in the protein ionic liquid; freezing the suspended cells between −20 to −212° C.; and removing at least 99% of water from the frozen suspended cells to make a cell powder. The cell powder may be reconstituted in Tris HCl buffer and mixed to obtain uniform cell suspension; and centrifuged to obtain cell pellet.

9 Claims, 10 Drawing Sheets
(10 of 10 Drawing Sheet(s) Filed in Color)
Specification includes a Sequence Listing.

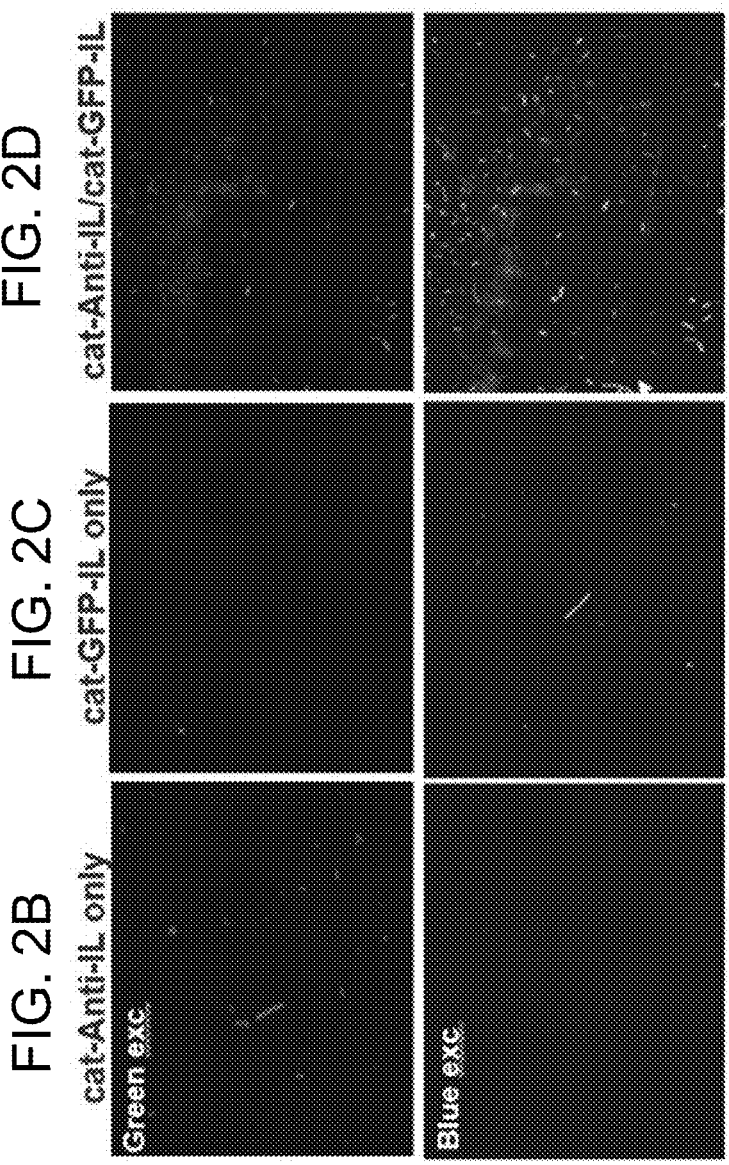
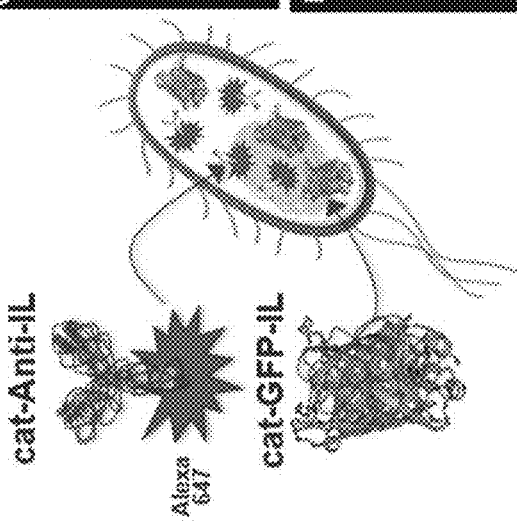

FIG. 3A
FIG. 3B
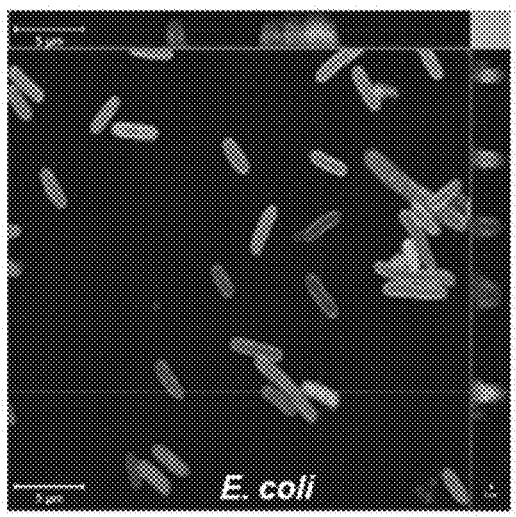
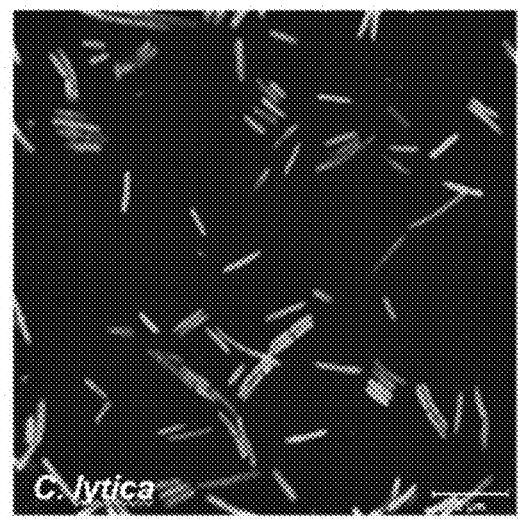
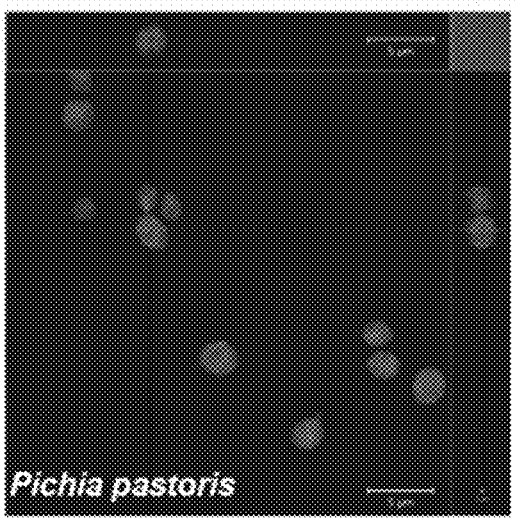
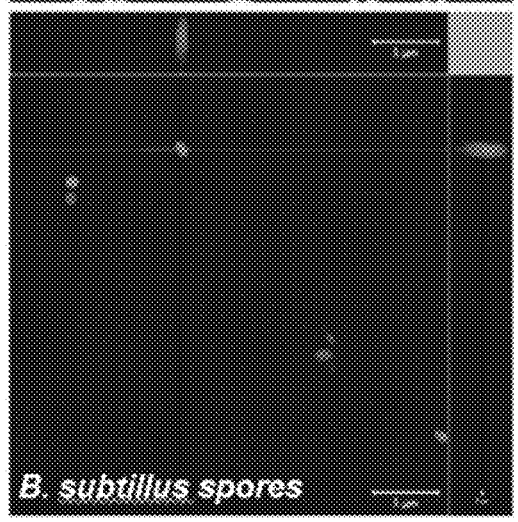
FIG. 3C
FIG. 3D

Au(CRRRRRRRRR)-iL

GFP-iL+Au(NTA)

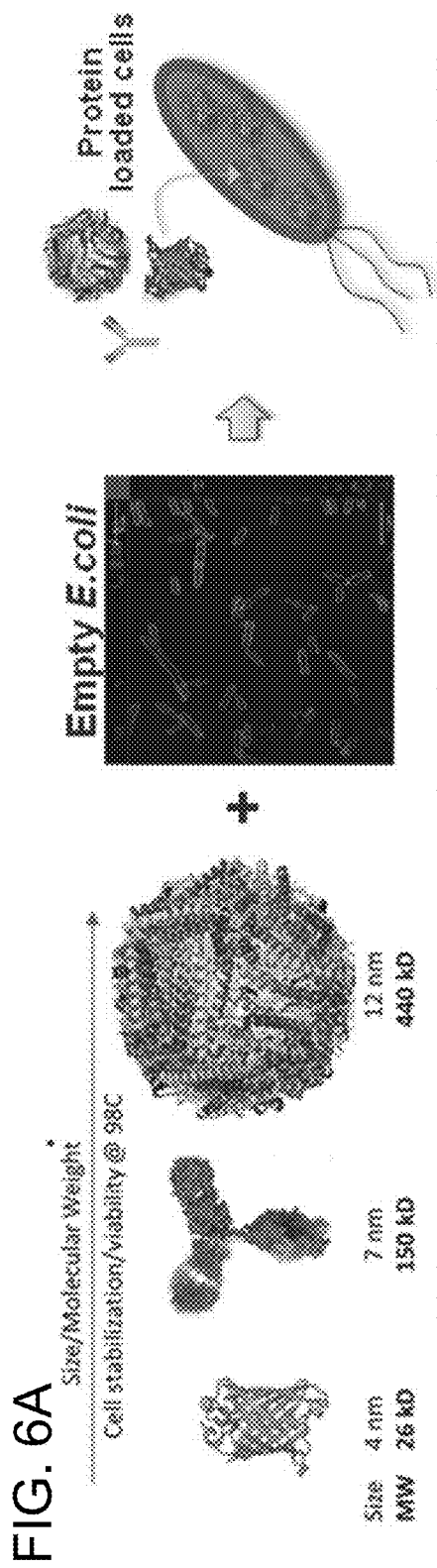
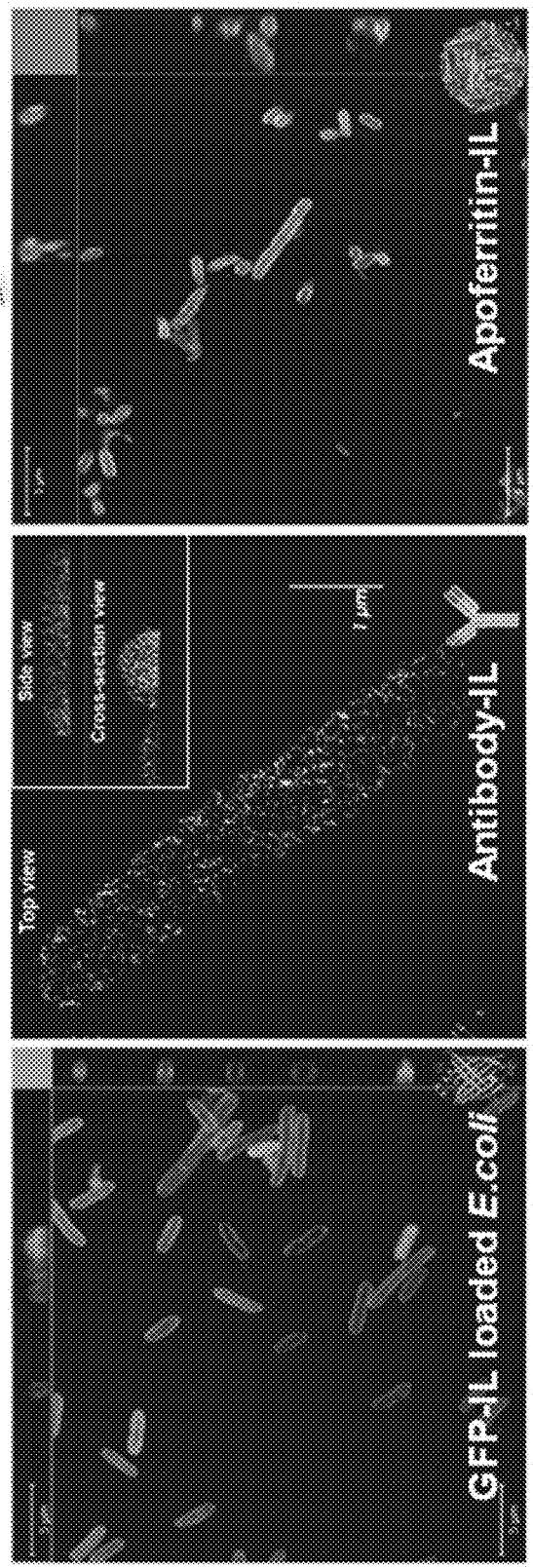
FIG. 6A
FIG. 6B
FIG. 6C
FIG. 6D

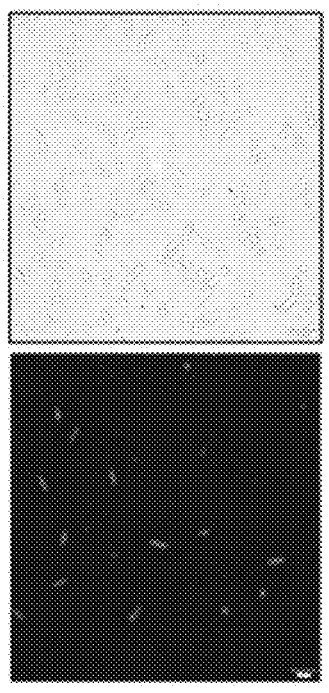
FIG. 8A
Untreated
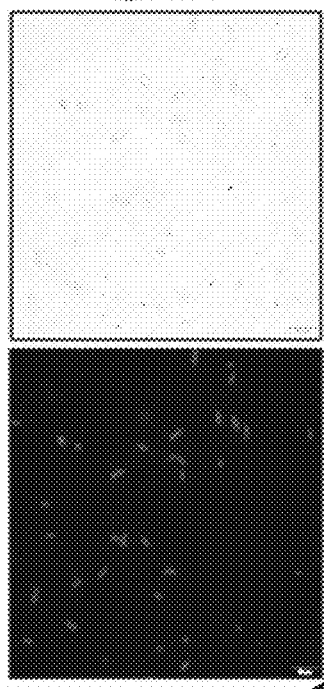
FIG. 8B
@100C
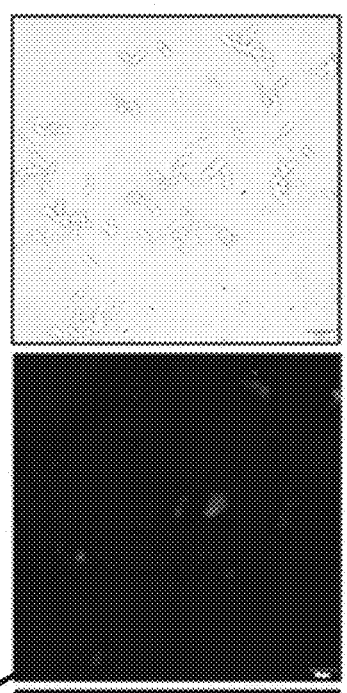
FIG. 8C
w/ GFP-IL
FIG. 8D
FIG. 8E
FIG. 8F
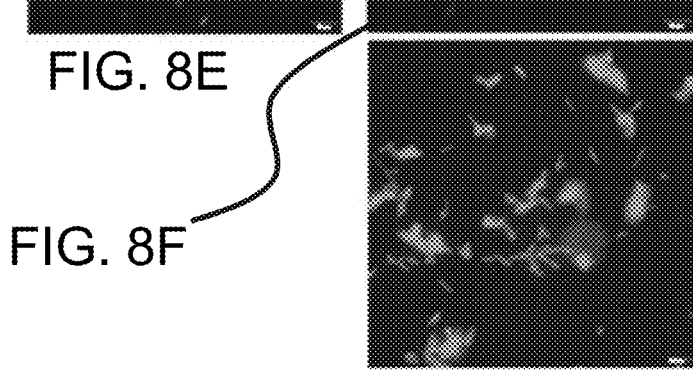
FIG. 8G

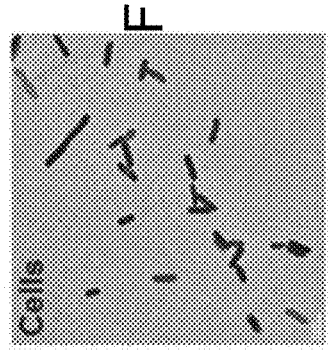
FIG. 9C
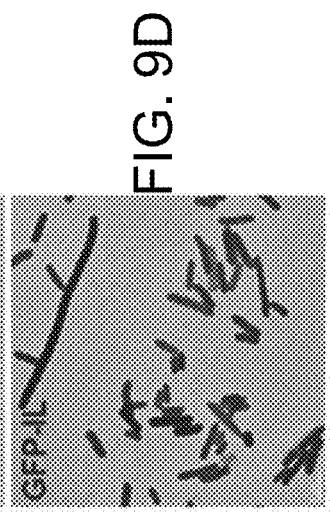
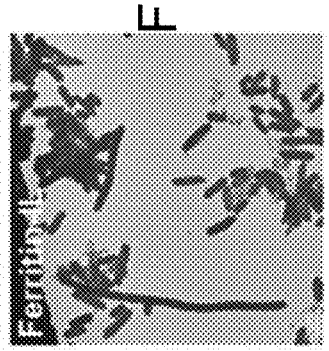
FIG. 9D
FIG. 9E
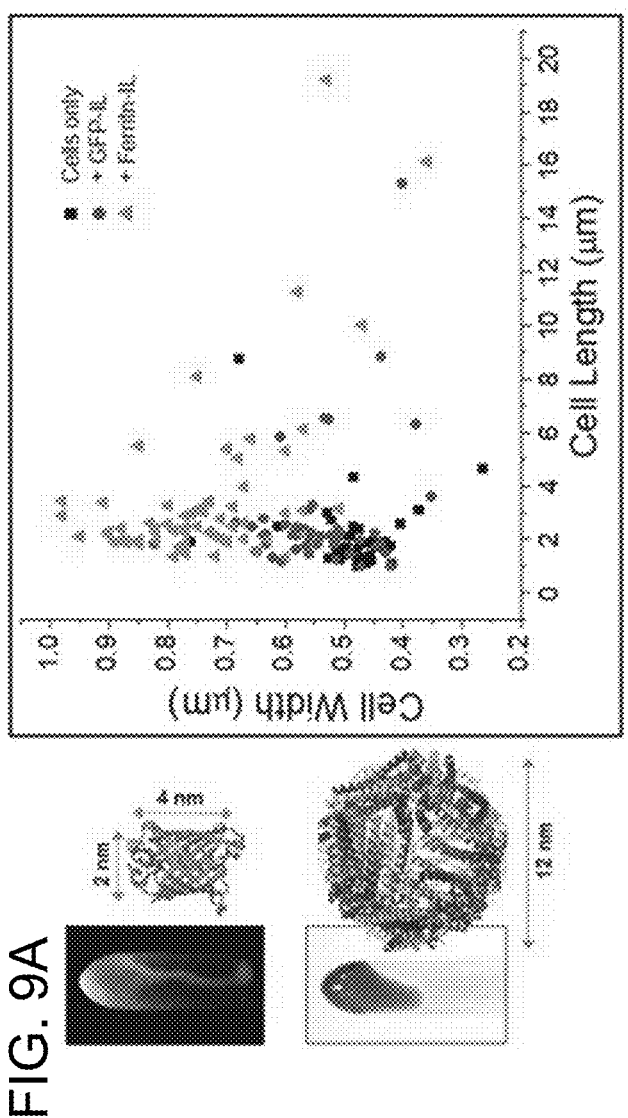
FIG. 9A
| | Avg. Length | Avg. Width | Cell volume | # of total protein |
|---|---|---|---|---|
| Cells | 2.15 µm | 0.48 µm | 0.49 µm³ | 3.0 × 10⁶ |
| +GFP-IL | 2.85 µm | 0.55 µm | 0.72 µm³ | 7.7 × 10⁶ |
| +Ferritin-IL | 3.58 µm | 0.74 µm | 1.58 µm³ | 4.2 × 10⁶ |
FIG. 9B

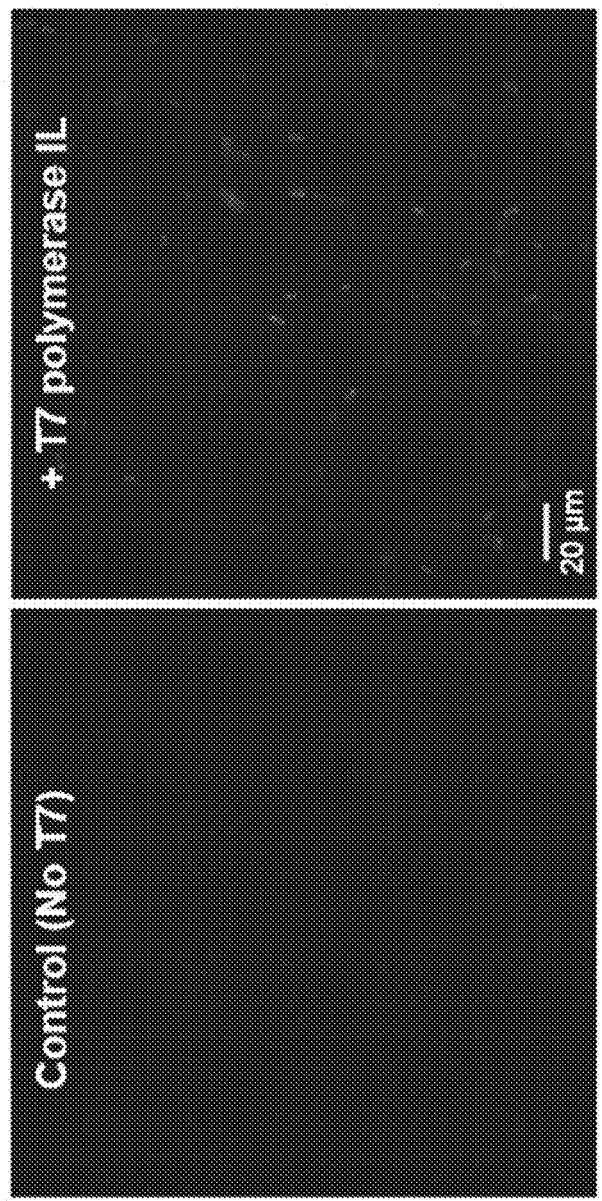

US 11,781,106 B1

INTRACELLULAR NON-GENETIC MODIFICATION OF MICROORGANISMS USING PROTEIN IONIC LIQUIDS

RIGHTS OF THE GOVERNMENT

The invention described herein may be manufactured and used by or for the Government of the United States for all governmental purposes without the payment of any royalty.

REFERENCE TO AN ELECTRIC SEQUENCE LISTING

The contents of the electronic sequence listing (AFD-2131_ST23.txt; Size: 832 bytes; and Date of Creation: Dec. 16, 2022) is herein incorporated by reference in its entirety.

FIELD OF THE INVENTION

The present invention relates generally to the transfection of microorganisms and, more particularly, to the intracellular delivery, loading, and transfection of microorganisms and/or bacterial spores with functional proteins.

BACKGROUND OF THE INVENTION

Microorganisms are routinely transformed with DNA plasmids by heat shocking or electroporation methods in order to perform recombinant protein expression, to change cell phenotype, and produce high value biological commodities. As a result, transformed bacteria or yeast acquire and retain permanent genetic modifications or genotypes that are passed along to all daughter cells irrespective of cell generation. Alternatively, the non-genetic modification of microorganisms at the protein level is much more challenging, but does not result in a permanent modification carried over to all cell generations. Consequently, the intracellular introduction of heterologous proteins inside microorganisms is not a current practice to our knowledge, nor is the existence of a universal protein transfection reagent for gram-negative bacteria. By comparison and as a point of reference, protein/DNA transfection reagents for mammalian cells are expensive, highly specialized, and toxic (i.e. LipofectamineTM, spherical nucleic acids, viruses). Notably, these rely on highly-specific cell-penetrating sequences or cationic lipid mixtures and the cell's natural ability to endocytose foreign protein objects in order to achieve protein/DNA transfection of cells. Consequently, it would be highly desirable to have the ability to controllably deliver and transport exogenous designer proteins inside bacteria, yeast, or spores. Such tools would expand the capabilities for synthetic biology (e.g. living inks), universal and inexpensive transfection agents for microorganisms, and enable temporary cell modifications.

SUMMARY OF THE INVENTION

The present invention overcomes the foregoing problems and other shortcomings, drawbacks, and challenges of the transfection of genetically tractable and intractable microorganisms with proteins for temporary manipulation. The disclosed use of protein ionic liquids represents the first non-genetic approach for modifying cells with proteins that lack permanent genetic modifications, and as a result, this invention eliminates the risk of accidental introduction of GMO's into the environment. While the invention will be described in connection with certain embodiments, it will be understood that the invention is not limited to these embodiments. To the contrary, this invention includes all alternatives, modifications, and equivalents as may be included within the spirit and scope of the present invention. The terms 'about' or 'approximately' are intended to indicate +/−10% or +/−10° C. of the stated values.

According to one embodiment of the present invention a method for transfecting microorganisms comprises inoculating a growth media consisting of at least one of sterile LB media and tryptic soy broth with microorganism cells (cells) consisting of at least one of $E.\ coli$ (DH5α), $C.\ lytica$, or $B.\ subtilus$, $Pichia\ pastoris$; growing the cells at between 28-40° C. to achieve a desired cell density; harvesting the cells; adding a protein ionic liquid consisting of at least one of GFP (green fluorescent protein) ionic liquid, cat-ferritin ionic liquid, cat-IgG antibody ionic liquid, and photosystem II ionic liquid to the cells; suspending the cells in the protein ionic liquid; freezing the suspended cells between −20 to −212° C.; and removing at least 99% of water from the frozen suspended cells to make a cell powder.

In a first variation of the invention, the cell powder may be reconstituted in Tris HCl buffer and mixed to obtain a uniform cell suspension; and centrifuged to obtain a cell pellet.

In another variation of the invention, the method may further comprise inoculating sterile LB growth media with at least one of $E.\ coli$ (DH5α), $C.\ lytica$, and $B.\ subtilus$; and growing at about 37° C.

In a further variation of the invention, the method may further comprise inoculating TSB, i.e. tryptic soy broth media, with Pichia pastoris; and growing at about 30° C.

In another variation of the invention, the method may further comprise harvesting the cells by centrifugation at 4500-8500 rpm for 2-10 min; removing the supernatant to obtain cell pellets.

In a further variation of the invention, the method may further comprise reconstituting water-free protein ionic liquid in deionized water; adding the protein ionic liquid to the cell pellets; re-suspending the cells in the protein ionic solution.

In another variation of the invention, the method may further comprise freezing the cells suspended in the protein ionic liquid solution at −20° C. to −212° C. in one or more of a conventional freezer, ultra-cold freezer, or by immersion in liquid nitrogen for 2-20 min.

In a further variation of the invention, the method may further comprise removing the water from the frozen mixture by one or more of lyophilization or a vacuum concentrator to dryness under vacuum.

In a another variation of the invention, the method may further comprise reconstituting the lyophilized powder in Tris HCl buffer and mixing to obtain uniform cell suspension; centrifuging at 4500-8500 rpm for 2-10 minutes to obtain a cell pellet; and removing supernatant from the cell pellet.

In a further variation of the invention, the method may further comprise washing cell pellet with 0.1 M heparin and pelleting; washing with 0.1 M Tris HCl and pelleting.

In a second embodiment of the invention a transfected microorganism comprises at least one of $E.\ coli$ (DH5α), $C.\ lytica$, $B.\ subtilus$, and $Pichia\ pastoris$ transfected with at least one of green fluorescent protein (GFP), ferritin, rabbit IgG antibodies, and photosystem II from spinach.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention. The patent or application file contains at least one drawing executed in color. Copies of this patent or patent application publication with color drawing(s) will be provided by the Office upon request and payment of the necessary fee.

FIGS. 2A-2G illustrate multiple protein transfection of DH5α E. coli cells (Puc19 plasmid) in a single step.

FIGS. 3A-3D present confocal microscopy images for transfection of different microorganisms with GFP ionic liquid.

FIGS. 6A-6D illustrate confocal microscopy and super resolution fluorescence images for protein ionic liquid transfection of E. coli with GFP, Antibody, and Apoferritin ionic liquids.

FIGS. 8A-8G presents membrane permeability assay of untreated E. coli cells with propidium iodide, cells heated at 100° C. for 10 min with propidium iodide, and cat-GFP-IL treated cells with propidium iodide.

FIGS. 9A-9E presents physical dimensions of E. coli cells by cell length and width after transfection with GFP and ferritin ionic liquids.

FIGS. 10A-10C present protein ionic liquid induced expression of fluorescent protein (MeoS) in DH5α E. coli cells transformed with MeoS-PST44 plasmid.

Figure 1A:
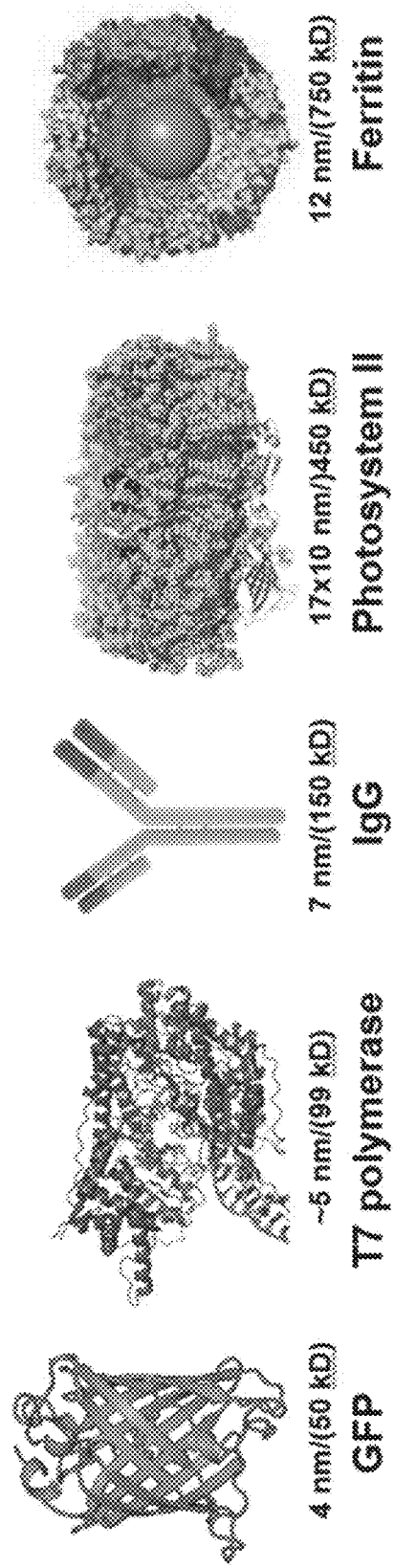
FIGS. 1A-1B present protein ionic liquid components for transfection of microorganisms with proteins.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. The term 'about' indicates +/−10% of the stated value, or +/−10° C., unless a different range is presented. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The invention provides for the intracellular delivery, loading, and transfection of microorganisms and/or bacterial spores with functional proteins. Uses for the disclosed method include the transfection of genetically tractable and intractable microorganisms with proteins for temporary manipulation of cell phenotype and proteome, modification and neutralization of bacterial spores, ruggedization of microorganisms for preservation and storage under extreme environmental conditions, and printing of living inks with minimal loss of viability.

The non-genetic modification of microorganisms at the proteome level is challenging, however, it does not result in a permanent modification carried over to all cell generations. Consequently, the intracellular modification/transfection of microorganisms with heterologous proteins is not a current practice to our knowledge, nor is the existence of a universal protein transfection reagent for gram-negative bacteria or yeast. Alternatively, protein ionic liquids may be used as general transfection agents to intracellularly load microorganisms with an assortment of proteins for temporary introduction of proteins inside cells. To date, this represents the first example of a non-genetic approach for temporarily modifying cells with proteins and eliminates the risk of GMOs.

The invention provides for the intracellular delivery, loading, and transfection of microorganisms and/or bacterial spores with functional proteins. Uses include transfection of genetically tractable and intractable microorganisms with proteins, temporary manipulation of cell phenotype and proteome, modification and neutralization of bacterial spores, preservation and storage under extreme environmental conditions, and printing of living inks.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

We exploited the solvent and transport properties of protein ionic liquids for the intracellular transfection of microorganisms (gram-negative bacteria and yeast) with functional proteins. A set of proteins ranging in size from 55 kD to 740 kD (see FIG. 1A) were converted into protein ionic liquids and delivered to the cell's cytoplasm at high protein concentrations. A 'high' protein concentration was determined qualitatively by fluorescence intensity, e.g. pixel brightness, of GFP in cells (see FIGS. 6A-6D) and by an overall increase in physical dimensions of cells after transfection process (see FIGS. 9A-9E). Protein ionic liquids serve as inexpensive and general transfection agents for delivering an assortment of functional proteins exhibiting a variety of molecular weights and geometries/quaternary structures to the cytoplasm of genetically tractable and intractable microorganisms; for temporarily changing cell phenotype and proteome via protein-targeted introduction of new cellular processes (e.g. cell division, light-harvesting phototrophic behavior); and as a means to temporarily control cell function (i.e. T7 polymerase driven transcription).

Protein ionic liquids are defined as cationized proteins wrapped by anionic polymers that form a charge neutral protein salt. After removal of water, the protein salt melts near room temperature to produce a highly viscous liquid. The benefits of proteins being converted into an ionic liquid state include high thermal stability, long shelf-life, and increased solubility in non-biological solvents. (See FIGS. 1A-1B) GFP, T7 RNA polymerase, ferritin, IgG antibodies, and photosystem II have been delivered to cell cytoplasm.

Figure 1B:
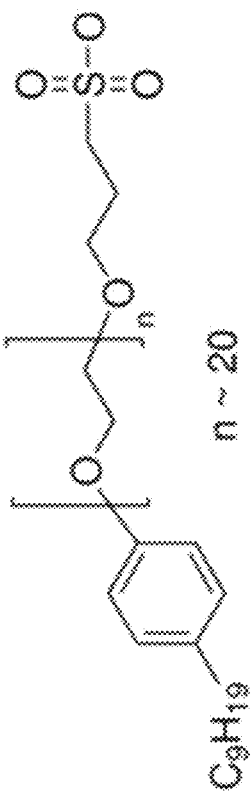

FIG. 1A depicts molecular structures of proteins used for transfection, and FIG. 1B depicts the chemical structure of anions used to balance positive charges on proteins.

FIG. 2A illustrates the molecular structures of cat-Anti-IL and cat-GFP-IL and cellular internalization. FIGS. 2B-2D present fluorescent images of cells transfected with cat-Anti-IL, cat-GFP-IL, and both simultaneously. Cells were dispersed in a reconstituted solution of protein ionic liquids, lyophilized to dryness, reconstituted in 0.1 M Tris buffer, centrifuged to obtain a cell pellet, washed with 0.1 M heparin, recentrifuged to obtain a pellet, reconstituted in buffer, and imaged on a glass slide. The top set of fluorescent images (FIGS. 2B-2D) show excitation of Alexa Fluor 647 conjugated to cat-Anti-IL using green excitation filters. The bottom set of images (FIGS. 2E-2G) show excitation of cat-GFP-IL using blue excitation.

The use of protein ionic liquids to introduce proteins inside microorganisms represents a non-genetic approach for temporarily modifying cells with proteins. For example, over successive cell division cycles, the original protein ionic liquid content of parental cells gets allocated to new generations of daughter cells, thereby, resulting in a proportional decrease in protein with each new generation until protein levels becomes undetectable. Additionally, multi-functional protein ionic liquids composed of two or more proteins (i.e. ferritin+antibodies; GFP+antibodies (see FIGS. 2A-2G)) offer the ability to simultaneously transfect microorganisms with high concentrations of two different proteins on demand and in a single transfection step. Protein ionic liquids also protect and minimize degradation of proteins by proteases in cytoplasm through protein stabilization. Importantly, this represents a non-genetic approach for modifying cells with proteins that lack permanent genetic modifications, and as a result, eliminates the risk of releasing GMOs into the environment.

Method

I. For intracellular delivery, transport, loading, and transfection of microorganisms, e.g. Gram-negative prokaryotes—E. coli and C. lytica; Eurkarotes—P. pastoris, with exogenous and heterologous proteins, e.g. water-free protein ionic liquids composed of cationized green fluorescent protein (cat-GFP), cationized ferritin (cat-ferritin), T7 RNA polymerase, or cationized Immunoglobulins (cat-IgG), and a stoichiometric amount of alkyl ether sulfonate ($C_9H_{19}C_6H_4$-$(OCH_2CH_2)_{20}O(CH_2)_3SO_3$) were reconstituted in water, mixed thoroughly with cells at an optical density of ~0.8 to ensure a homogeneous suspension of cells, frozen @-80° C., and lyophilized for 1-2 hours to remove all water content, i.e. at least 99% of water content.

Molecular structures of each protein and the anion chemical structure are presented in FIGS. 1A-1B. Stoichiometric amount of anions is the number of anions needed to balance all of the positive charges on cationized protein. As an example of reconstitution in water, ~5 mg of protein ionic liquids were reconstituted in 50 µL of double deionized water at room temperature. Mixing was achieved by pipetting and dispensing cell pellet in solution several times with a calibrated volumetric pipette in order to suspend cells in protein ionic liquid. Mixing can also be done by gently tapping or swirling tube with cell. Optical density (OD) is measured by absorbance at 600 nm on a UV-Vis spectrophotometer. The cells may be at about –20° C. or with liquid nitrogen at about –196° C. The acceptable freezing range would be about –20 to –196° C. Lyophilization is analogous to freeze drying and used to remove water by sublimation.

II. After lyophilization, cells treated with cat-GFP ionic liquid (or cat-ferritin ionic liquid or cat-IgG ionic liquid) were reconstituted in 0.01 M Tris-HCl, centrifuged, e.g. centrifuged and pelleted at about 8200 rpm for about 2-5 minutes, e.g. about 3 minutes, washed with heparin, centrifuged, and washed with 0.01 M Tris-HCl to remove excess heparin and cat-GFP (or cat-ferritin or cat-IgG).

III. E.coli, C. lytica, or P. pastoris cells treated with GFP ionic liquids (or cat-ferritin ionic liquid or cat-IgG ionic liquid) were characterized by confocal fluorescence microscopy to confirm protein internalization and for viability by measuring growth curves (OD600 nm) or number of colony-forming units. 'OD' represents optical density and is universally used to measure cell density in liquid culture by absorbance at 600 nm. By confocal fluorescence microscopy, cells showed the presence of internalized GFP in *E. coli, C. lytica, P. pastoris,* and *B. subtilis* endospores (See FIGS. 3A-3D, respectively). Also, after treatment with GFP ionic liquids, cells showed less than ~5% loss in viability (data not shown). Cells treated with cat-ferritin ionic liquid exhibited about 12% viability loss, cells treated with cat-IgG ionic liquid are expected to be between 5-15% viability loss.

FIGS. 3A-3D present confocal microscopy images for transfection of different microorganisms with GFP ionic liquid (IL). Cells or spores were mixed with reconstituted GFP-IL in water, frozen at –80° C., lyophilized to dryness, reconstituted back in 0.1 M Tris HCl, centrifuged and washed with heparin. Top images (FIGS. 3A-3B) present *E. coli* and *C. lytica* cells transfected with GFP ionic liquid were stained with a FM4-64 cell membrane dye (orange fluorescence). The bottom images (FIGS. 3C-3D) present *Pichia pastoris* and *B. subtilis* spores transfected with GFP ionic liquid.

Figure 4:
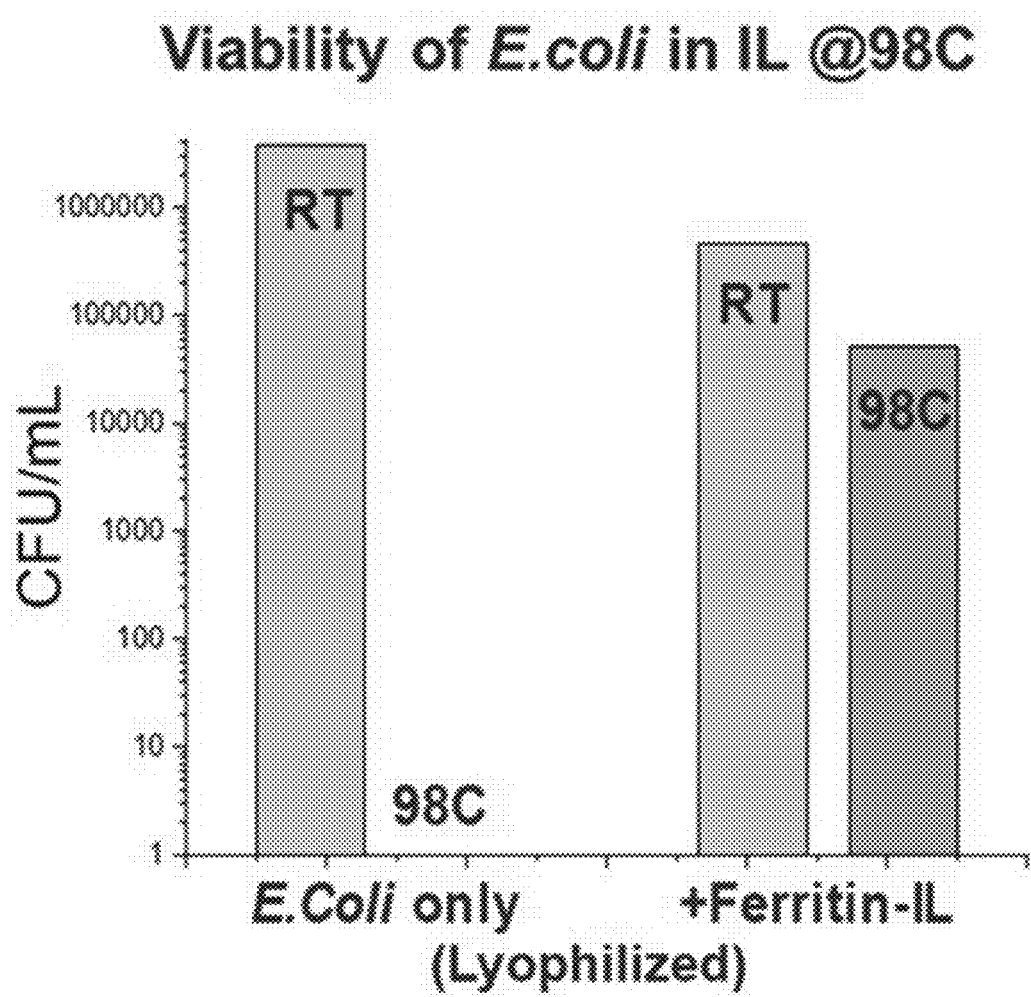
FIG. 4 Cell viability of lyophilized E. coli only (Control) and lyophilized E. coli transfected with ferritin ionic liquid at room temperature and after heating at 98° C. for 30 minutes.

FIG. 4 presents cell viability of lyophilized *E. coli* only (Control, on left) and lyophilized *E. coli* transfected with ferritin ionic liquid at room temperature and after heating at 98° C. for 30 minutes. After exposure to temperature, the cells were reconstituted in deionized water, plated on LB agar (e.g. Luria-Bertani medium) plates with ampicillin by serial dilutions, grown at 37° C. for 18 hours, and counted for number of colonies per mL. The *E. coli* control (left) at 98° C. were non-viable, whereas, *E. coli* in ferritin ionic liquid were viable at 98° C.

Figure 5B:
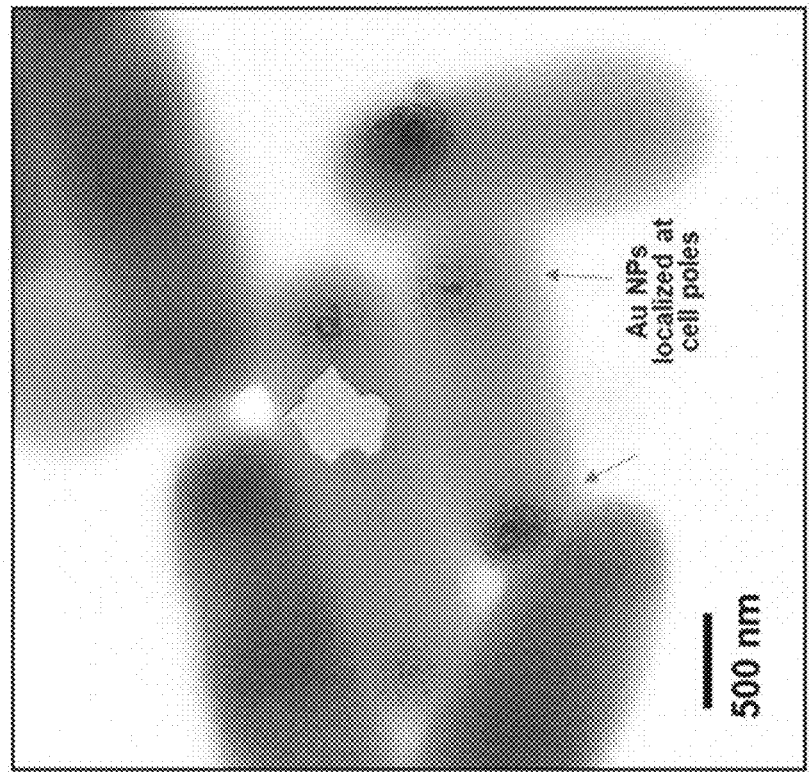
FIGS. 5A-5B present TEM images of E. coli cells transfected with gold nanoparticles using protein ionic liquids (Left, FIG. 5A) E. coli transfected with Au(Ni-nitrilotriacetic acid) or Au(NTA) bound to histidine tagged GFP-IL (Right, FIG. 5B) E. coli transfected with peptide functionalized (SEQ ID NO: 1) Au nanoparticle ionic liquids.
Figure 5A:
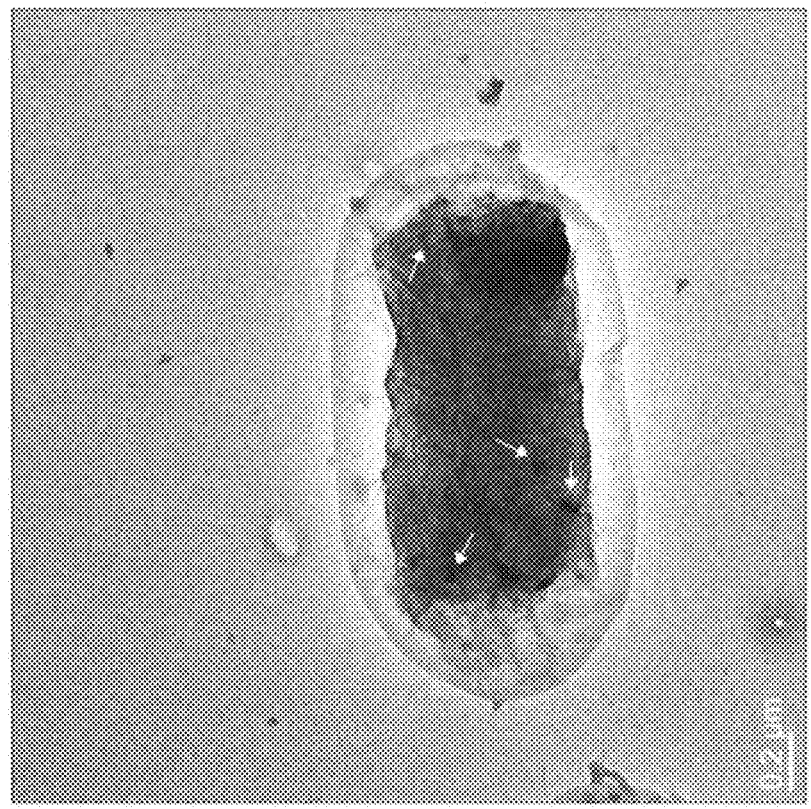

FIG. 5 TEM images of *E. coli* cells transfected with gold nanoparticles using protein ionic liquids (FIG. 5A) *E. coli* transfected with Au(Ni-nitrilotriacetic acid) or Au(NTA) bound to histidine tagged GFP-IL (FIG. 5B) *E. coli* transfected with peptide functionalized Au nanoparticle ionic liquids. Nanoparticle ionic liquids were created by functionalizing 10 nm Au pre-formed Au nanoparticle colloids with peptides (Cys-Arg-Arg-Arg-Arg-Arg-Arg-Arg-Arg-Arg-Arg-Arg-Arg) (SEQ ID NO: 1) and balancing charges with anions. After transfection, cells were treated with $I_2/I^-$ in order to etch exterior Au nanoparticles.

Alternatives: Water-free protein ionic liquids integrated with small inorganic nanoparticles (gold, quantum dots, iron oxide) of 2-15 nm may be used to transfect the cytoplasm of microorganisms with optically, catalytically, or magnetically responsive nanomaterials. FIGS. 5A-5B present gold 5 nm nanoparticles. The controlled internalization of nanomaterials within microorganisms may be used as a biosensor to remotely monitor internal cellular processes. Additionally, protein ionic liquids may be made with highly complex biocomposites such as ribosomes, peroxisomes, or nanomaterials. In total, this greatly increases the ability to temporarily modify cell functions.

FIGS. 6A-6D present confocal microscopy and super resolution fluorescence images for the protein ionic liquid transfection of *E. coli* with GFP, Antibody, and Apoferritin ionic liquids. FIG. 6A presents a comparison of the molecular sizes of proteins used to prepare protein ionic liquids for transfection of a non-transformed DH5α strain of E. coli (image with red stained outer membrane). FIG. 6B presents a confocal image of GFP ionic liquid loaded E. coli and stained with FM4-64 membrane. FIG. 6C presents a super resolution image of antibody ionic liquid loaded E. coli after transfection. FIG. 6D presents a confocal image of E. coli loaded with apoferritin ionic liquid conjugated with Alex Fluor 647 dye and stained with FM4-64 membrane dye.

Figure 7:
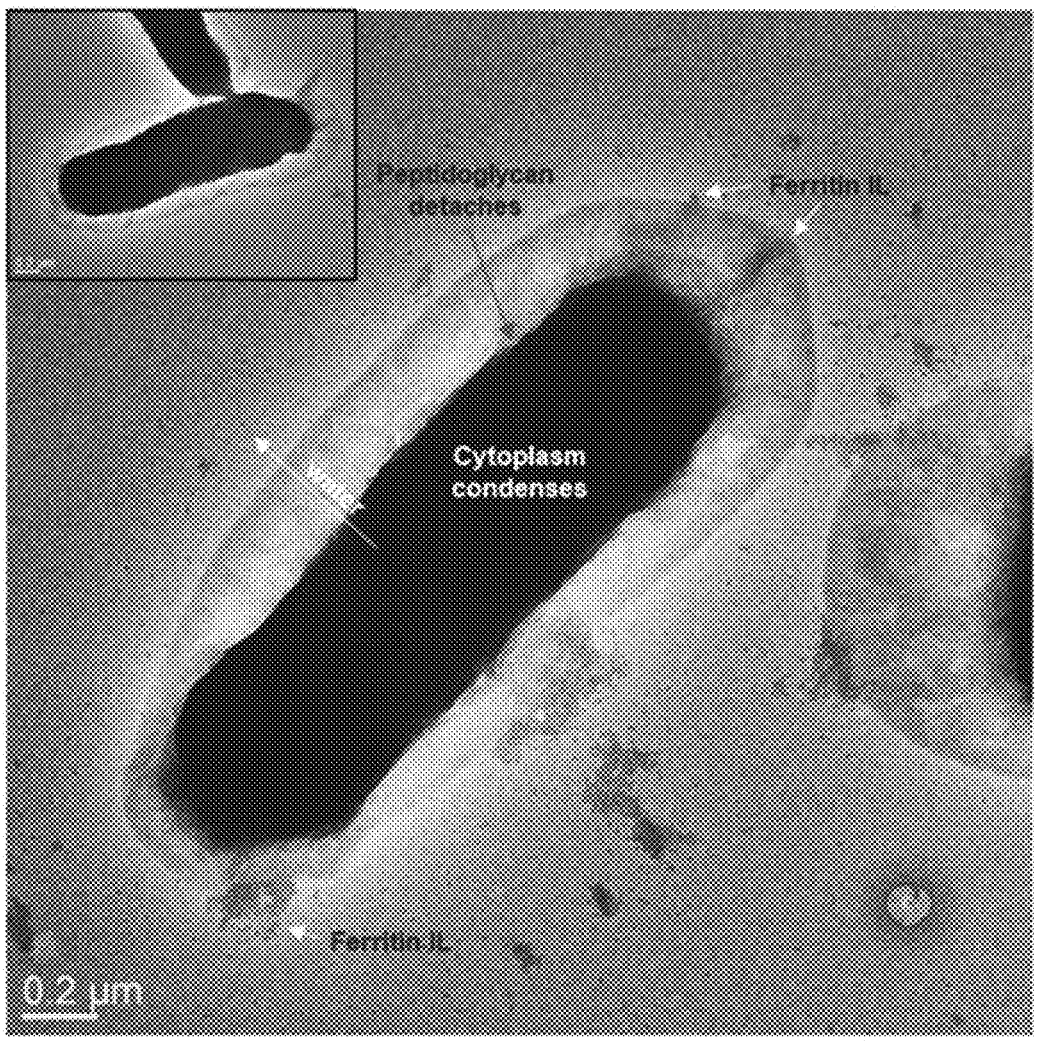
FIG. 7 presents a TEM image of E. coli cells transfected with ferritin ionic liquid and washed with heparin.

FIG. 7 presents a TEM image of E. coli cells transfected with ferritin ionic liquid and washed with heparin. The inset (upper left corner) shows another region of E. coli cells transfected with ferritin ionic liquid. The labelled arrows indicate formation of channels in the outer membrane and periplasm filled with ferritin molecules. Additional labelled arrows and labels indicate cell plasmolysis induced by ferritin ionic liquid.

FIGS. 8A-8G present membrane permeability assays of untreated E. coli cells with propidium iodide (FIGS. 8A, 8D), cells heated at 100° C. for 10 min with propidium iodide (FIGS. 8B, 8E), and cat-GFP-IL treated cells with propidium iodide (FIGS. 8C, 8F, 8G).

9A-9E present a comparison of the physical dimensions of E. coli cells by cell length and width after transfection with GFP and ferritin ionic liquids. Scatter plot and table (FIGS. 9A-9B) present size/dimensions of individual cells treated with ferritin or GFP ionic liquids after transfection process measured from the TEM images (FIGS. 9C-9E).

10A-10C present protein ionic liquid induced expression of fluorescent protein (MeoS) in DH5α E. coli cells transformed with MeoS-PST44 plasmid. FIG. 10A illustrates the internalization of T7 polymerase ionic liquid followed by DNA transcription and protein expression. FIGS. 10B-10C present fluorescent images of control cells (No cat-T7 ionic liquid, FIG. 10B) and cells transfected with cat-T7 ionic liquid (FIG. 10C) after 4 hours of growth in LB media at 37° C.

Example Procedure for Synthesis of Water-Free Protein Ionic Liquid:

Add 1 to 5 mg of protein, i.e. green fluorescent protein (GFP), ferritin, rabbit IgG antibodies, or photosystem II from spinach, to 1 mL of 0.1 M MES buffer, i.e. 2-(N-morpholino) ethanesulfonic acid, pH 5.0 to obtain a protein concentration of 1 mg/mL to 5 mg/mL.

In a separate microfuge tube, add 10-40 µL of 3-dimethylaminopropylyamine (Sigma Aldrich) to 100 µL of doubly deionized water and adjust to a pH of 5-6 using ~25-120 µL of 6 M HCl.

Add the total volume of pH-adjusted 3-dimethylaminopropylamine to protein in MES buffer.

In a separate microfuge tube also dissolve 0.25 mg-1 mg of EDC (1-ethyl-3-(3-dimethylaminopropyl) carbodiimide hydrochloride) in 100 µL of doubly deionized water. Add the EDC solution to protein and dimethylaminopropylamine in MES buffer.

Incubate for 2-6 hours at room temperature to ensure coupling of 3-dimtheylaminopropylamine to antibody.

After 2-6 hours, dialyze the cationized protein from excess coupling reagents using a slide-A-Lyzer dialysis cassette (3500 MWCO 3 mL volume) (Thermo Fisher) in 2 L of double deionized water (18.2 MOhms), while stirring on a magnetic stir plate at 4° C. in a refrigerator. Perform 4 to 5 water changes over 2 days to ensure removal of excess reagents.

Remove cationized protein from dialysis cassette and centrifuge at 14,000 rpm for 5 minutes to remove any cross-linked and/or precipitated proteins.

Measure the zeta potential of cationized protein (Optional) to ensure cationization of the proteins.

Dissolve 4 mg-20 mg of an anion, e.g. poly(ethylene glycol) 4-nonylphenyl 3-sulfopropyl ether potassium salt (Sigma Aldrich), into 100 µL of doubly deionized water and add to the cationized protein to balance charges and form protein-polymer complex, i.e. modified antibody/anion pair.

Freeze the modified antibody/anion pair in liquid nitrogen and Lyophilize to complete dryness, i.e. at least 99% of water removed, for ~18 hours on a lyophilizer or vacuum concentrator.

Gently warm lyophilized powder to ~35° C.-65° C. to form a viscous protein ionic liquid on a hot plate, heating block, or oven for 5-30 minutes.

The protein ionic liquid may be used for the transfection of microorganisms and spores.

Example Procedure for Transfection of Microorganisms With Water-Free Protein Ionic Liquids:

10 mL of sterile LB media is inoculated with frozen stocks (they are kept frozen at −80° C. for long term storage) of E. coli (DH5α), C. lytica, or B. subtilus and grown overnight (~18 hrs) at about 37° C. at 200 rpm in a shaking incubator to reach maximum cell density. 10 mL of TSB, i.e. tryptic soy broth media, media is inoculated with Pichia pastoris and grown overnight at about 30° C. at 200 rpm in a shaking incubator to reach maximum cell density. These growth conditions are not critical but represent optimal experimentally-determined growth conditions. The cells may be grown at lower temperatures (e.g. room temperature), and without shaking, but at the cost of slower growth.

50 µL-10 mL of cells are harvested by centrifugation at 8200 rpm for 5 min. After centrifugation, the supernatant is removed and discarded to obtain cell pellets. Centrifugation increases cell pelleting, but is not critical. Another option is to leave cells sitting unperturbed. Eventually, they will settle to bottom by gravity but after much longer times. The goal is to obtain a cell pellet and to remove the media.

1 mg-20 mg of water free protein ionic liquid comprising, e.g. green fluorescent protein (GFP), ferritin, rabbit IgG antibodies, or photosystem II from spinach, is reconstituted in 50 µL-5 mL of double deionized water and added to cell pellets.

Cells are gently resuspended in protein ionic solution by pipetting solution up and down in pipette tip several times or until cell pellet is completely resuspended.

Cells suspended in protein ionic liquid solution are frozen at −20° C. to −212° C. in a conventional freezer, ultra-cold freezer, or by immersion in liquid nitrogen for 2 min-20 min.

Water is removed from the frozen mixture by lyophilization or on a vacuum concentrator to dryness under vacuum for 2-6 hours. Transfection occurs at point of protein ionic liquid addition to cells and then is maximized during lyophilization. Lyophilization creates an increasing concentration gradient that helps to fully drive the proteins inside the cells.

Lyophilized powder is reconstituted in 100 µL-1 mL of 0.1 M Tris HCl buffer and mixed to obtain uniform cell suspension. Cells are centrifuged at 8200 rpm for 5 min to obtain cell pellet. Supernatant is removed from cell pellet.

Optimally, the cell pellet is washed with 0.1 M heparin and pelleted. Cells are re-suspended in heparin by gentle shaking and pipetting. After heparin wash, cells are washed with 0.1 M Tris HCl and pelleted. Washing steps are optional, but necessary for imaging and confirmation of protein internalization. For ruggedization or shelf-life studies, the cells are not washed.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method for non-genetic modification of microorganisms, comprising:
    inoculating a growth media consisting of at least one of sterile Luria-Bertani (LB) media and tryptic soy broth (TSB) with microorganism cells (cells) consisting of at least one of DH5α strain of *Escherichia coli*, *Cellulophaga lytica*, *Bacillus subtilis*, or *Pichia pastoris*;
    growing the cells at between 28-40° C. to achieve a desired cell density;
    harvesting the cells;
    making a water-free protein ionic liquid, the method comprising
        adding green fluorescent protein (GFP) to a 2-(N-morpholino) ethanesulfonic acid buffer solution to obtain a protein solution having a protein concentration of 1-5 mg/mL,
        in a separate vessel, adding 3-dimethylaminopropylyamine to deionized water and adjust to a pH of 5-6;
        mixing the 3-dimethylaminopropylyamine solution with the protein solution;
        dissolving EDC (1-ethyl-3-(3-dimethylaminopropyl) carbodiimide hydrochloride) in deionized water, and adding the EDC solution to the protein solution;
        incubating the protein solution to couple the 3-dimethylaminopropylyamine to the protein and create a solution of cationized proteins;
        removing excess reagents from the cationized protein solution;
        dissolving an anion comprising poly(ethylene glycol) 4-nonylphenyl 3-sulfopropyl ether potassium salt into deionized water and adding to the cationized protein solution to form modified protein/anion pairs;
        lyophilizing the cationized protein solution to remove at least 99% of water from the modified protein/anion pairs to form a lyophilized powder; and
        warming the lyophilized powder between —35° C.-65° C. to form a water free protein ionic liquid;
    reconstituting 1 mg-20 mg of the water free protein ionic liquid in 50 μL-5 mL deionized water;
    adding the protein ionic liquid to the cells to transfect the cells;
    suspending the cells in the protein ionic liquid;
    freezing the suspended cells between −20 to −212° C.; and
    removing at least 99% of water from the frozen suspended cells to make a cell powder.

2. The method for non-genetic modification of microorganisms of claim 1, comprising:
    reconstituting the cell powder in 0.1 M Tris HCl buffer and mixing to obtain uniform cell suspension; and
    centrifuging to obtain cell pellet.

3. The method for non-genetic modification of microorganisms of claim 2, further comprising:
    washing cell pellet with 0.1 M heparin and pelleting;
    washing with 0.1M Tris HCl and pelleting.

4. The method for non-genetic modification of microorganisms of claim 1, further comprising:
    inoculating sterile LB growth media with at least one of DHα strain of *Escherichia coli*, *Cellulophaga lytica*, and *Bacillus subtilis*; and
    growing at about 37° C.

5. The method for non-genetic modification of microorganisms of claim 1, further comprising:
    inoculating TSB media, with Pichia pastoris; and
    growing at about 30° C.

6. The method for non-genetic modification of microorganisms of claim 1, further comprising:
    harvesting the cells by centrifugation at 4500-8500 rpm for 5 min;
    removing the supernatant to obtain cell pellets.

7. The method for non-genetic modification of microorganisms of claim 1, further comprising:
    freezing the cells suspended in the protein ionic liquid solution at −20° C. to −212° C. in one or more of a conventional freezer, ultra-cold freezer, or by immersion in liquid nitrogen for 2-20 min.

8. The method for non-genetic modification of microorganisms of claim 7, further comprising:
    removing the water from the frozen mixture by one or more of lyophilization or a vacuum concentrator to dryness under vacuum.

9. The method for non-genetic modification of microorganisms of claim 1, further comprising:
   reconstituting the cell powder in Tris HCl buffer and mixing to obtain uniform cell suspension;
   centrifuging at 4500-8500 rpm for 2-10 minutes to obtain a cell pellet; and
   removing supernatant from the cell pellet.

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: chemically synthesized using amino acids and
      coupling reagents

<400> SEQUENCE: 1

Cys Arg Arg Arg Arg Arg Arg Arg Arg Arg Arg Arg Arg
1               5                   10
```